United States Patent
Chen et al.

[11] Patent Number: 6,103,731
[45] Date of Patent: *Aug. 15, 2000

[54] IMIDAZOL[1,5-C]QUINAZOLINES; A NEW CLASS OF GABA BRAIN RECEPTOR

[75] Inventors: Paul Chen, North Branford; Alan Hutchison, Madison; Guolin Cai, Guilford, all of Conn.

[73] Assignee: Neurogen Corporation, Branford, Conn.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/131,971

[22] Filed: Aug. 11, 1998

Related U.S. Application Data

[63] Continuation of application No. 08/614,878, Mar. 13, 1996, Pat. No. 5,792,766.
[51] Int. Cl.[7] .................. A61K 31/519; C07D 487/04
[52] U.S. Cl. .................. 514/267; 514/243; 514/248; 514/250; 544/179; 544/180; 544/184; 544/234; 544/250
[58] Field of Search .................. 514/267, 207; 544/250, 251

[56] References Cited

U.S. PATENT DOCUMENTS 5,792,766  9/1998  Chen et al. .................. 514/253

*Primary Examiner*—Richard L. Raymond
*Assistant Examiner*—Venkataraman Balasubramanian
*Attorney, Agent, or Firm*—McDonnell Boechnen Hulbert & Berghoff; Steven J. Sarussi

[57] ABSTRACT

Disclosed are compounds of compounds of the formula:

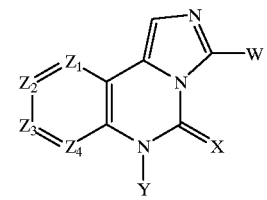

or the pharmaceutically acceptable nontoxic salts thereof wherein:

X is oxygen, $H_2$ or sulfur

Y is hydrogen, or optionally substituted alkyl, alkenyl, (substituted)arylalkyl, aryl or heteroaryl, or a carbonyl group substituted with alkyl, cycloalkyl, aryl, or amino groups;

W is alkyl, arylalkyl or heteroarylalkyl, where each aryl group is optionally substituted with up to two groups; or W is aryl, thienyl, pyridyl or heteroaryl, each of which is optionally substituted; and $Z_1$, $Z_2$, $Z_3$, and $Z_4$ independently represent nitrogen or $C-R_1$ where $R_1$ is hydrogen, halogen, hydroxy, amino, or phenyl or pyridyl optionally mono- or independently disubstituted with halogen, hydroxy, lower alkyl, or lower alkoxy, which compounds are highly selective agonists, antagonists or inverse agonists for GABAa brain receptors or prodrugs of agonists or inverse agonists for GABAa brain receptors. These compounds are useful in the diagnosis and treatment of anxiety, sleep, and seizure disorders, overdose with benzodiazepine drugs, and enhancement of memory.

12 Claims, No Drawings

IMIDAZOL[1,5-C]QUINAZOLINES; A NEW CLASS OF GABA BRAIN RECEPTOR

This is a continuation of application Ser. No.08/614,878, filed Mar. 13, 1996, now U.S. Pat. No. 5,792,766.

BACKGROUND OF THE INVENTION

1. Field of the Invention

This invention relates to novel imidazo[1,5-c] quinazolines which selectively bind to GABAa receptors. This invention also relates to pharmaceutical compositions comprising such compounds. It further relates to the use of such compounds in treating anxiety, sleep and seizure disorders, and overdoses of benzodiazepine-type drugs, and enhancing alertness.

2. Description of the Related Art

γ-Aminobutyric acid (GABA) is regarded as one of the major inhibitory amino acid transmitters in the mammalian brain. Over 40 years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. In most regions of the brain, GABA is associated with local inhibitory neurons and only in two regions is GABA associated with longer projections. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA responses is a major site of action for a number of structurally unrelated compounds capable of modifying postsynaptic responses to GABA. Depending on the mode of interaction, these compounds are capable of producing a spectrum of activities (either sedative, anxiolytic, and anticonvulsant, or wakefulness, seizures, and anxiety).

1,4-Benzodiazepines continue to be among the most widely used drugs in the world. Principal among the benzodiazepines marketed are chlordiazepoxide, diazepam, flurazepam, and triazolam. These compounds are widely used as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. The benzodiazepines were capable of enhancing presynaptic inhibition of a monosynaptic ventral root reflex, a GABA-mediated event (Schmidt et al., 1967, Arch. Exp. Path. Pharmakol. 258: 69–82). All subsequent electrophysiological studies (reviewed in Tallman et al. 1980, Science 207: 274–81, Haefley et al., 1981, Handb. Exptl. Pharmacol. 33: 95–102) have generally confirmed this finding, and by the mid-1970s, there was a general consensus among electrophysiologists that the benzodiazepines could enhance the actions of GABA.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior.

Studies on the mechanistic nature of these interactions depended on the demonstration of a high-affinity benzodiazepine binding site (receptor). Such a receptor is present in the CNS of all vertebrates phylogenetically newer than the boney fishes (Squires & Braestrup 1977, Nature 166: 732–34, Mohler & Okada, 1977, Science 198: 854–51, Mohler & Okada, 1977, Br. J. Psychiatry 133: 261–68). By using tritiated diazepam, and a variety of other compounds, it has been demonstrated that these benzodiazepine binding sites fulfill many of the criteria of pharmacological receptors; binding to these sites in vitro is rapid, reversible, stereospecific, and saturable. More importantly, highly significant correlations have been shown between the ability of benzodiazepines to displace diazepam from its binding site and activity in a number of animal behavioral tests predictive of benzodiazepine potency (Braestrup & Squires 1978, Br. J. Psychiatry 133: 249–60, Mohler & Okada, 1977, Science 198: 854–51, Mohler & Okada, 1977, Br. J. Psychiatry 133: 261–68). The average therapeutic doses of these drugs in man also correlate with receptor potency (Tallman et al. 1980, Science 207: 274–281).

In 1978, it became clear that GABA and related analogs could interact at the low affinity (1 mM) GABA binding site to enhance the binding of benzodiazepines to the clonazepam-sensitive site (Tallman et al. 1978, Nature, 274: 383–85). This enhancement was caused by an increase in the affinity of the benzodiazepine binding site due to occupancy of the GABA site. This data was interpreted to mean that both GABA and benzodiazepine sites were allosterically linked in the membrane as part of a complex of proteins. For a number of GABA analogs, the ability to enhance diazepam binding by 50% of maximum and the ability to inhibit the binding of GABA to brain membranes by 50% could be directly correlated. Enhancement of benzodiazepine binding by GABA agonists is blocked by the GABA receptor antagonist (+) bicuculline; the stereoisomer (−) bicuculline is much less active (Tallman et al., 1978, Nature, 274: 383–85).

Soon after the discovery of high affinity binding sites for the benzodiazepines, it was discovered that a triazolopyridazine could interact with benzodiazepine receptors in a number of regions of the brain in a manner consistent with receptor heterogeneity or negative cooperativity. In these studies, Hill coefficients significantly less than one were observed in a number of brain regions, including cortex, hippocampus, and striatum. In cerebellum, the triazolopyridazine interacted with benzodiazepine sites with a Hill coefficient of 1 (Squires et al., 1979, Pharma. Biochem. Behav. 10: 825–30, Klepner et al. 1979, Pharmacol. Biochem. Behav. 11: 457–62). Thus, multiple benzodiazepine receptors were predicted in the cortex, hippocampus, striatum, but not in the cerebellum.

Based on these studies, extensive receptor autoradiographic localization studies were carried out at a light microscopic level. Although receptor heterogeneity has been demonstrated (Young & Kuhar 1980, J. Pharmacol. Exp. Ther. 212: 337–46, Young et al., 1981 J. Pharmacol Exp. ther 216: 425–430, Niehoff et al. 1982, J. Pharmacol. Exp. Ther. 221: 670–75), no simple correlation between localization of receptor subtypes and the behaviors associated with the region has emerged from the early studies. In addition, in the cerebellum, where one receptor was predicted from binding studies, autoradiography revealed heterogeneity of receptors (Niehoff et al., 1982, J. Pharmacol. Exp. Ther. 221: 670–75).

A physical basis for the differences in drug specificity for the two apparent subtypes of benzodiazepine sites has been demonstrated by Sieghart & Karobath, 1980, Nature 296: 285–87. Using gel electrophoresis in the presence of sodium dodecyl sulfate, the presence of several molecular weight receptors for the benzodiazepines has been reported. The receptors were identified by the covalent incorporation of radioactive flunitrazepam, a benzodiazepine which can covalently label all receptor types. The major labeled bands have molecular weights of 50,000 to 53,000, 55,000, and 57,000 and the triazolopyridazines inhibit labeling of the slightly higher molecular weight forms (53,000, 55,000, 57,000) (Seighart et al. 1983, Eur. J. Pharmacol. 88: 291–99).

At that time, the possibility was raised that the multiple forms of the receptor represent "isoreceptors" or multiple allelic forms of the receptor (Tallman & Gallager 1985, Ann. Rev. Neurosci. 8, 21–44). Although common for enzymes, genetically distinct forms of receptors have not generally been described. As we begin to study receptors using specific radioactive probes and electrophoretic techniques, it is almost certain that isoreceptors will emerge as important in investigations of the etiology of psychiatric disorders in people.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into , β, γ, δ, ε, and provide a molecular basis for the GABAa receptor heterogeneity and distinctive regional pharmacology (Shivvers et al., 1980; Levitan et al., 1989). The γ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

Drugs that interact at the GABAa receptor can possess a spectrum of pharmacological activities depending on their abilities to modify the actions of GABA. For example, the beta-carbolines were first isolated based upon their ability to inhibit competitively the binding of diazepam to its binding site (Nielsen et al., 1979, Life Sci. 25: 679–86). The receptor binding assay is not totally predictive about the biological activity of such compounds; agonists, partial agonists, inverse agonists, and antagonists can inhibit binding. When the beta-carboline structure was determined, it was possible to synthesize a number of analogs and test these compounds behaviorally. It was immnediately realized that the beta-carbolines could antagonize the actions of diazepam behaviorally (Tenen & Hirsch, 1980, Nature 288: 609–10). In addition to this antagonism, beta-carbolines possess intrinsic activity of their own opposite to that of the benzodiazepines; they become known as inverse agonists.

In addition, a number of other specific antagonists of the benzodiazepine receptor were developed based on their ability to inhibit the binding of benzodiazepines. The best studied of these compounds is an imidazodiazepine (Hunkeler et al., 1981, Nature 290: 514–516). This compound is a high affinity competitive inhibitor of benzodiazepine and beta-carboline binding and is capable of blocking the pharmacological actions of both these classes of compounds. By itself, it possesses little intrinsic pharmacological activity in animals and humans (Hunkeler et al., 1981, Nature 290: 514–16; Darragh et al., 1983, Eur. J. Clin. Pharmacol. 14: 569–70). When a radiolabeled form of this compound was studied (Mohler & Richards, 1981, Nature 294: 763–65), it was demonstrated that this compound would interact with the same number of sites as the benzodiazepines and beta-carbolines, and that the interactions of these compounds were purely competitive. This compound is the ligand of choice for binding to GABAa receptors because it does not possess receptor subtype specificity and measures each state of the receptor.

The study of the interactions of a wide variety of compounds similar to the above has led to the categorizing of these compounds. Presently, those compounds possessing activity similar to the benzodiazepines are called agonists. Compounds possessing activity opposite to benzodiazepines are called inverse agonists, and the compounds blocking both types of activity have been termed antagonists. This categorization has been developed to emphasize the fact that a wide variety of compounds can produce a spectrum of pharmacological effects, to indicate that compounds can interact at the same receptor to produce opposite effects, and to indicate that beta-carbolines and antagonists with intrinsic anxiogenic effects are not synonymous. A biochemical test for the pharmacological and behavioral properties of compounds that interact with the benzodiazepine receptor continues to emphasize the interaction with the GABAergic system. In contrast to the benzodiazepines, which show an increase in their affinity due to GABA (Tallman et al., 1978, Nature 274: 383–85, Tallman et al., 1980, Science 207: 274–81), compounds with antagonist properties show little GABA shift (i.e., change in receptor affinity due to GABA) (Mohler & Richards 1981, Nature 294: 763–65), and the inverse agonists actually show a decrease in affinity due to GABA (Braestrup & Nielson 1981, Nature 294: 472–474). Thus, the GABA shift predicts generally the expected behavioral properties of the compounds.

Various compounds have been prepared as benzodiazepine agonists and antagonists. For example, PCT publications WO 92/22552 and WO 9317025 as well as several other references disclose compounds useful in treating disorders of the central nervous system.

WO 92/22552 teaches compounds of the Formula A:

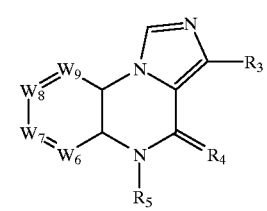

Wherein $R_3$=H, alkyl, cycloalkyl, hydroxy, alkoxy, amino, aminocarbonyl, alkoxycarbonyl, heterocyclic ring or aryl etc;

$R_4$=$H_2$ or H and OH or H and heterocyclic ring with $R_5$;

$R_5$=carbonyl, alkanoyl, aminocarbonyl, hydroxyaminocarbonyl or thienyl etc;

$W_6$=N or —$CR_6$;

$R_6$=H, halogen, —CN, —$NO_2$, —CF3, —OCF3, —$CH_2CH_2OH$, cycloalkyl, alkoxycarbonyl, alkyl, aminocarbonyl, hydroxyaminocarbonyl or thienyl etc;

$W_7 = N$ or $—CR_7$,  $R_7 = R_6$;

$W_8 = N$ or $—CR_8$,  $R_8 = R_6$; and $W_9 = N$ or $—CR_9$,  $R_9 = R_6$.

WO 9317025 discloses compounds of Formula B:

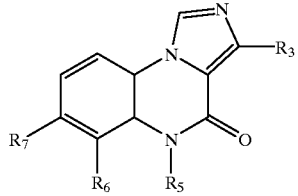

Wherein $R_3$ is

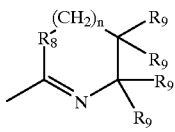

—Aryl —COAryl —CSR$_{11}$

—Aryl=aryl or heteroaryl with various substituents;

$R_5$=alkyl, cycloalkyl, alkyl-cycloalkyl, alkenyl, $(CH_2)_n$-Aryl, $(CH_2)_m$ or alkoxy; n=0–4; m=2–4;

$R_6$ and $R_7$=H, F, Br, Cl, I, CN, $NO_2$, alkoxy, alkoxycarbonyl or aminocarbonyl etc.;

$R_8$=O, S, —NH, —NCH$_3$, —N-alkyl-cycloalkyl or —NCHO;

$R_9$=H, alkyl, phenyl; and $R_{11}$=H, alkyl, cycloalkyl, alkyl-cycloalkyl or (CH2)n-Aryl.

Several references teach compounds of Formula C:

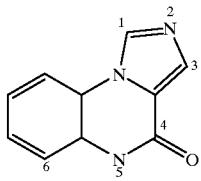

For example, U.S. Pat. No. 4,999,353 and EP 368,652 disclose 4-oxo-imidazo[1,5-a]quinoxalines useful as anxiolytics and hypnotics with an oxadiazole at position 3 and tert-butyl at position 5.

European Patent 320,136 discloses 4-oxoimidazo[1,5-a]-quinoxaline compounds useful as anxiolytic and hypnotic agents, containing oxadiazole or ester substituents at the 3-position and hydrogen or halogen substituents at the 6-position. The ring atom at position 6 may be carbon or nitrogen.

European Patent 344,943 discloses a group of imidazo[1,5-a] quinoxaline compounds, useful as anxiolytic and anti-convulsant agents, having a methyl with different substituents at the 5-position.

U.S. Pat. No. 5,116,841 and PCT publication WO 91/07407 disclose 4-oxoimidazo[1,5-a]quinoxalines useful as anxiolytics and hypnotics with isoxazoles at position 3.

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in enhancing alertness, treatment of seizure, anxiety, and sleep disorders and treatment of benzodiazepine overdoses. Accordingly, a broad embodiment of the invention is directed to compounds of Formula I:

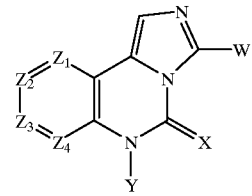

or the pharmaceutically acceptable nontoxic salts thereof wherein:

X is oxygen, $H_2$ or sulfur

Y is hydrogen, alkyl, alkenyl, (substituted)arylalkyl, alkoxycarbonyl, acyl, aroyl, alkoxyalkyl, alkoxy, alkylamino-carbonyl, cycloalkylaminocarbonyl, aryl or heteroaryl each of which is optionally substituted with halogen, lower alkyl, amino lower alkyl, or lower alkoxy;

W is alkyl, arylalkyl or heteroarylalkyl, where each aryl group is optionally substituted with up to two groups independently selected from halogen, alkyl, alkoxy, trifluoromethyl, lower alkyl, amino lower alkyl, mono- or dialkyl amino where each alkyl is independently lower alkyl; or W is aryl, thienyl, pyridyl or heteroaryl, each of which is optionally substituted with up to two groups independently selected from halogen, hydroxy, lower alkyl, or lower alkoxy having 1–6 carbon atoms; amino, mono- or dialkylamino where each alkyl is independently lower alkyl, and $Z_1$, $Z_2$, $Z_3$, and $Z_4$ independently represent nitrogen or C-R$_1$ where $R_1$ is hydrogen, halogen, hydroxy, amino, or phenyl or pyridyl optionally mono- or independently disubstituted with halogen, hydroxy, lower alkyt, or lower alkoxy.

The iraidazo[1,5-c]quinazolines of the invention interact with a GABA binding site, the benzodiazepines (BDZ) receptor. This interaction results in the pharmacological activities of these compounds.

The compounds of the invention are highly selective agonists or inverse agonists for GABAa brain receptors or prodrugs of agonists or inverse agonists for GABAa brain receptors. These compounds are useful in the diagnosis and treatment of anxiety, sleep, and seizure disorders, overdose of benzodiazepine drugs, and enhancement of memory.

DETAILED DESCRIPTION OF THE INVENTION

In addition to compounds of general formula I described above, the invention encompasses compounds of general formula IA:

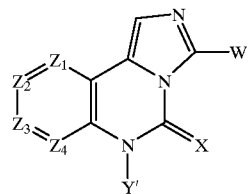

IA

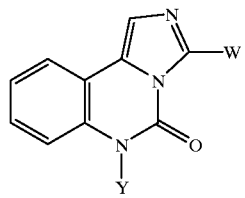

II or the pharmaceutically acceptable nontoxic salts thereof wherein:

X is oxygen, $H_2$ or sulfur

Y' is hydrogen, alkyl, alkenyl, (substituted)arylaLkyl, alkoxy, alkoxyalkyl, or aryl or heteroaryl each of which is optionally substituted with halogen, lower alkyl, amino lower alkyl, or lower alkoxy; or Y' is a group of the formula:

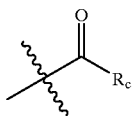

where $R_c$ represents alkoxy, lower alkyl, aryl, heteroaryl, mono- or dialkylamino, cycloalkylamino;

W is alkyl, arylalkyl or heteroarylalkyl, where each aryl group is optionally substituted with up to two groups independently selected from halogen, alkyl, alkoxy, trifluoromethyl, lower alkyl, amino lower alkyl, mono- or dialkyl amino where each alkyl is independently lower alkyl; or W is aryl, thienyl, pyridyl or heteroaryl, each of which is optionally substituted with up to two groups independently selected from halogen, hydroxy, lower alkyl, or lower alkoxy having 1–6 carbon atoms; amino, mono- or dialkylamino where each alkyl is independently lower alkyl, and $Z_1$, $Z_2$, $Z_3$, and $Z_4$ independently represent nitrogen or C-$R_1$ where $R_1$ is hydrogen, halogen, hydroxy, amino, or phenyl or pyridyl optionally mono- or independently disubstituted with halogen, hydroxy, lower alkyl, or lower alkoxy.

Preferred compounds of formula I are those where $Z_1$, $Z_2$, $Z_3$, and Z4 represent C—H, Y is lower alkyl, acyl, aroyl, alkylaminocarbonyl, or cycloalkylaminocarbonyl, and W is optionally substituted aryl. More preferably, W represents optionally substituted phenyl.

Preferred compounds of formula IA are those where $Z_1$, $Z_2$, $Z_3$, and $Z_4$ represent C—H, Y' is lower alkyl, acyl, benzoyl, dialkylaminocarbonyl, or cycloalkylaminocarbonyl, and W is optionally substituted aryl. More preferably, W represents optionally substituted phenyl, and Y' is —$COR_c$ where —$COR_c$ represents acetyl, propionyl, benzoyl, piperidinylcarbonyl, diethylaminocarbonyl, dimethylaminocarbonyl, or morpholinylcarbonyl.

In addition, the present invention encompasses compounds of Formula II:

wherein

Y is hydrogen, alkyl, alkenyl, (substituted)arylalkyl, alkoxy, alkoxyalkyl, or aryl or heteroaryl each of which is optionally substituted with halogen, lower alkyl, amino lower alkyl, or lower alkoxy; or Y is a group of the formula:

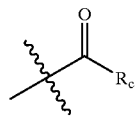

where $R_c$ represents alkoxy, lower alkyl, aryl, heteroaryl, mono- or dialkylamino, cycloalkylalino; and W is alkyl, arylalkyl or heteroarylalkyl, where each aryl group is optionally substituted with up to two groups independently selected from halogen, alkyl, alkoxy, trifluoromethyl, lower alkyl, amino lower alkyl, mono- or dialkyl amino where each alkyl is independently lower alkyl; or W is aryl, thienyl, pyridyl or heteroaryl, each of which is optionally substituted with up to two groups independently selected from halogen, hydroxy, lower alkyl, or lower alkoxy having 1–6 carbon atoms; amino, mono- or dialkylamino where each alkyl is independently lower alkyl.

Particularly preferred compounds according to Formula II are those where W represents phenyl, or alkoxyphenyl where the phenyl group is optionally halogenated. The most particularly preferred alkoxyphenyl derivatives are the 3- and 4-alkoxyphenyl, in particular the 3- and 4-methoxyphenyl derivatives of Formula II.

The present invention also encompasses compounds of Formula III:

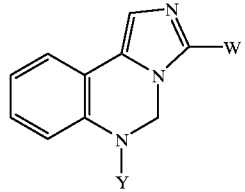

III wherein

Y is hydrogen, alkyl, alkenyl, (substituted)arylalkyl, alkoxy, alkoxyalkyl, or aryl or heteroaryl each of which is optionally substituted with halogen, lower alkyl, amino lower alkyl, or lower alkoxy; or Y is a group of the formula:

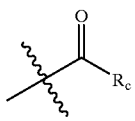

were $R_c$ represents alkoxy, lower alkyl, aryl, heteroaryl, mono- or dialkylamino, cycloalkylarnino; and W is alkyl, arylalkyl or heteroarylalkyl, where each aryl group is optionally substituted with up to two groups independently selected from halogen, alkyl, alkoxy, trifluoromethyl, lower alkyl, amino lower alkyl, mono- or dialkyl amino where each alkyl is independently lower alkyl; or W is aryl, thienyl, pyridyl or heteroaryl, each of which is optionally substituted with up to two groups independently selected from halogen, hydroxy, lower alkyl, or lower alkoxy having 1–6 carbon atoms; amino, mono- or dialkylamino where each alkyl is independently lower alkyl.

Particularly preferred compounds according to Formula III are those where W represents phenyl, or alkoxyphenyl where the phenyl group is optionally halogenated. The most particularly preferred alkoxyphenyl derivatives are the 3- and 4-alkoxyphenyl, in particular the 3- and 4-methoxyphenyl derivatives of Formula III.

In addition, the present invention encompasses compounds of Formula IV:

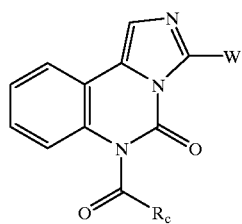

IV wherein $R_c$ represents alkoxy, lower alkyl, aryl, heteroaryt, mono- or dialkylamino, cycloalkylarnino; and W is alkyl, arylalkyl or heteroarylalkyl, where each aryl group is optionally substituted with up to two groups independently selected from halogen, alkyl, alkoxy, trifluoromethyl, lower alkyl, amino lower alkyl mono- or dialkyl amino where each alkyl is independently lower alkyl; or W is aryl, thienyl, pyridyl or heteroaryl, each of which is optionally substituted with up to two groups independently selected from halogen, hydroxy, lower alkyl, or lower alkoxy having 1–6 carbon atoms; amino, mono- or dialkylamino where each alkyl is independently lower alkyl.

Particularly preferred compounds according to Formula IV are those where W represents phenyl, or alkoxyphenyl where the phenyl group is optionally halogenated. The most particularly preferred alkoxyphenyl derivatives are the 3- and 4-alkoxyphenyl, in particular the 3- and 4-methoxyphenyl derivatives of Formula IV.

In addition, the present invention encompasses compounds of Formnula V:

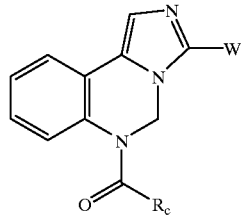

V wherein $R_c$ represents alkoxy, lower alkyl, aryl, heteroaryl, mono- or dialkylamino, cycloalkylamino; and W is alkyl, arylalkyl or heteroarylalkyl, where each aryl group is optionally substituted with up to two groups independently selected from halogen, alkyl, alkoxy, trifluoromethyl, lower alkyl, amino lower alkyl, mono- or dialkyl amino where each alkyl is independently lower alkyl; or W is aryl, thienyl, pyridyl or heteroaryl, each of which is optionally substituted with up to two groups independently selected from halogen, hydroxy, lower alkyl, or lower alkoxy having 1–6 carbon atoms; amino, mono- or dialkylamino where each alkyl is independently lower alkyl.

Particularly preferred compounds according to Formula V are those where W represents penyl, or alkoxyphenyl where the phenyl group is optionally halogenated. The most particularly preferred alkoxyphenyt derivatives are the 3- and 4-alkoxyphenyl, in particular the 3- and 4-methoxyphenyl derivatives of Formula V.

In addition, the present invention encompasses compounds of Formula VI:

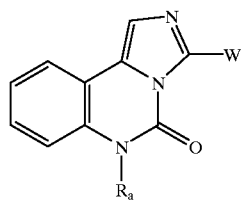

VI wherein $R_a$ represents hydrogen, alkyl, alkenyl, (substituted) arylalkyl, alkoxy, alkoxyalkyl, or aryl or heteroaryl each of which is optionally substituted with halogen, lower alkyl, amino lower alkyl, or lower alkoxy; and W is alkyl, arylalkyl or heteroarylalkyl, where each aryl group is optionally substituted with up to two groups independently selected from halogen, alkyl, alkoxy, trifluoromethyl, lower alkyl, amino lower alkyl, mono- or dialkyl amino where each alkyl is independently lower alkyl; or W is aryl, thienyl, pyridyl or heteroaryl, each of which is optionally substituted with up to two groups independently selected from halogen, hydroxy, lower alkyl, or lower alkoxy having 1–6 carbon atoms; amino, mono- or dialkylamino where each alkyl is independently lower alkyl.

In addition, the present invention encompasses compounds of Formula VII:

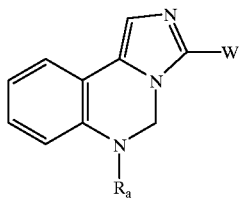

VII wherein $R_a$ represents hydrogen, alkyl, alkenyl, (substituted) arylalkyl, alkoxy, alkoxyalkyl, or aryl or heteroaryl each of which is optionally substituted with halogen, lower alkyl, amino lower alkyl, or lower alkoxy; and W is alkyl, arylalkyl or heteroarylalkyl, where each aryl group is optionally substituted with up to two groups independently selected from halogen, alkyl, alkoxy, trifluoromethyl, lower alkyl, amino lower alkyl, mono- or dialkyl amino where each alkyl is independently lower alkyl; or W is aryl, thienyl, pyridyl or heteroaryl, each of which is optionally substituted with up to two groups independently selected from halogen, hydroxy, lower alkyl, or lower alkoxy having 1–6 carbon atoms; amino, mono- or dialkylamino where each alkyl is independently lower alkyl.

The present invention also encompasses compounds of Formula VIII:

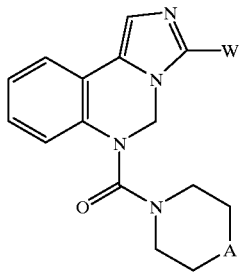

VIII wherein

A is oxygen, $CH_2$, —$(CH_2)_2$— or NH; and

W is alkyl, arylalkyl or heteroarylalkyl, where each aryl group is optionally substituted with up to two groups independently selected from halogen, alkyl, alkoxy, trifluoromethyl, lower alkyl, amino lower alkyl, mono- or dialkyl amino where each alkyl is independently lower alkyl; or W is aryl, thienyl, pyridyl or heteroaryl, each of which is optionally substituted with up to two groups independently selected from halogen, hydroxy, lower alkyl, or lower alkoxy having 1–6 carbon atoms; amino, mono- or dialkylamino where each alkyl is independently lower alkyl.

Preferred compounds according to Formula VIII are those where A is oxygen or nitrogen. Particularly preferred compounds of Formula VIII are those where A is oxygen, and W represents phenyl, or alkoxyphenyl where the phenyl group is optionally halogenated. More particularly preferred compounds of Formula VIII are those where the alkoxyphenyl group is an optionally halogenated 3- or 4-alkoxyphenyl group, in particular an optionally halogenated 3- or 4-methoxyphenyl group.

Other preferred compounds of Formula VIII are those where A is $CH_2$ or —$(CH_2)_2$—, and W represents thienyl, phenyl or alkoxy phenyl where the phenyl group is optionally halogenated. More preferred compounds of Formula VIII are those where A is methylene or ethylene and W is 2- or 3- thienyl or W is 3- or 4-methoxyphenyl.

Still other particularly preferred compounds of Formula VIII are those where A is $CH_2$, and W represents thienyl. Yet other preferred compounds of Formula VIII are those where A is ethylene and W is alkoxyphenyl, preferably methoxyphenyl.

As noted above, the compounds of the invention are highly selective agonists, antagonists or inverse agonists for GABAa brain receptors or prodrugs of agonists or inverse agonists for GABAa brain receptors. These compounds are useful in the diagnosis and treatment of anxiety, sleep, and seizure disorders, overdose with benzodiazepine drugs, and enhancement of memory.

Representative compounds of the present invention, which are encompassed by Formula I, include, but are not limited to the compounds in Table I and their pharmaceutically acceptable salts. Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

The following numbering system is used herein to identify positions on the 5,6-dihydro-6-imidazo[1,5-c] quinazoline portion of the compounds of the invention:

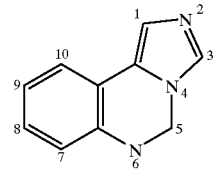

By aryl or "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy.

By heteroaryl is meant 5, 6, or 7 membered aromatic ring systems having at least one and up to four hetero atoms selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be substituted with, e.g., halogen, lower alkyl, lower alkoxy, lower alkylthio, trifluoromethyl, lower acyloxy, aryl, heteroaryl, and hydroxy.

Examples of various aryl and heteroaryl groups are shown in Chart D of published International Application WO 93/17025.

By alkyl and lower alkyl is meant straight and branched chain alkyl groups having from 1–6 carbon atoms. Specific non-limiting examples of alkyl groups are methyl, ethyl, propyl, isopropyl, n-butyl, isobutyl, tert-butyl, sec-butyl, neopentyl and n-pentyl.

By lower alkoxy and alkoxy is meant straight and branched chain alkoxy groups having from 1–6 carbon atoms.

By halogen is meant fluorine, chlorine, bromine and iodine.

As used herein, —CORc represents a group of the formula:

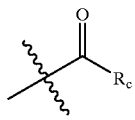

where $R_c$ is defined above.

In the compounds of the invention, preferred Y groups include the following:

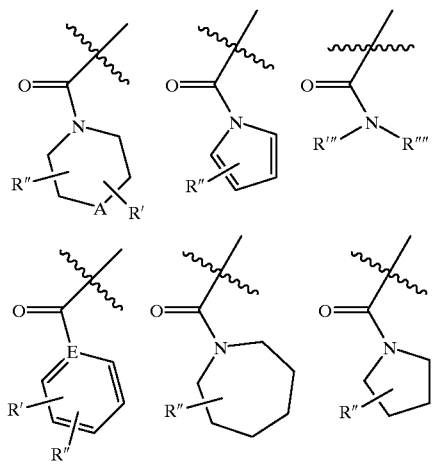

where A is NH, CH$_2$ or oxygen; E is oxygen or nitrogen; R' and R" independently represent hydrogen, halogen, hydroxy, alkyl or lower alkoxy; and R'" and R"" independently represent lower alkyl.

In the above Y groups of the invention, preferred R' and R" groups are hydrogen, halogen, or alkoxy.

More preferred Y groups of the invention include the following:

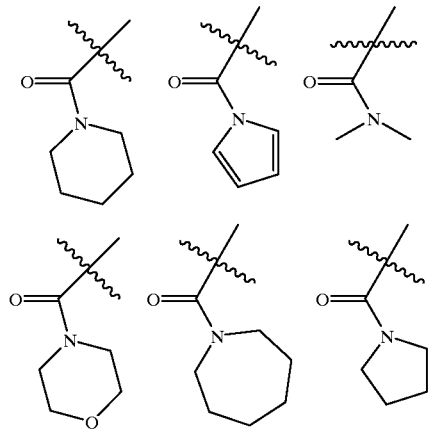

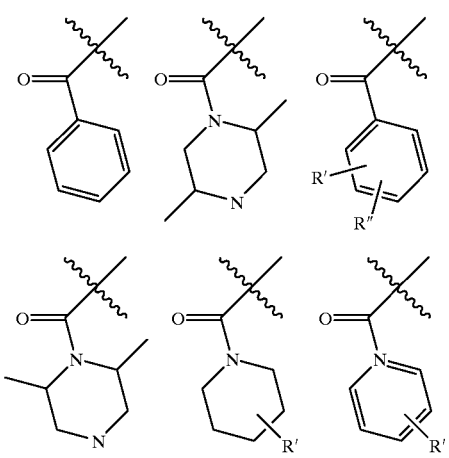

where R' and R" are as defined immediately above.

Representative examples of imidazo[1,5-c]quinazolines according to the invention are shown in Table 1 below.

TABLE 1

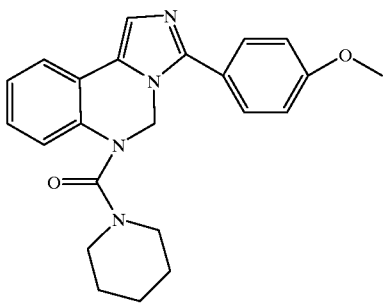

Compound 1

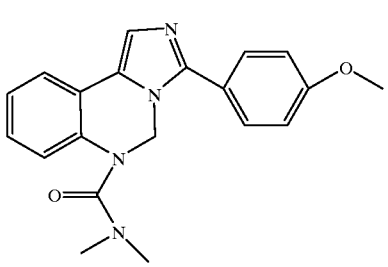

Compound 2

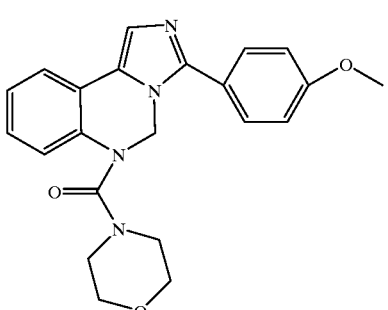

Compound 3

TABLE 1-continued

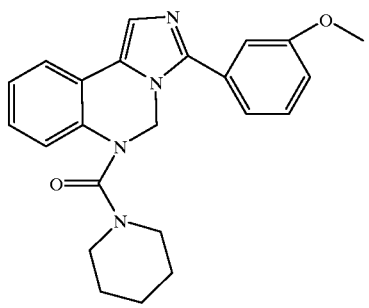
Compound 16

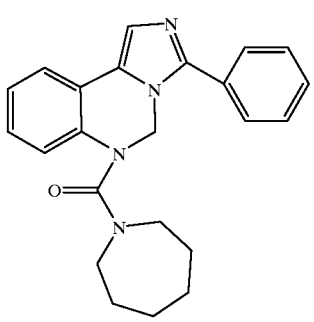
Compound 18

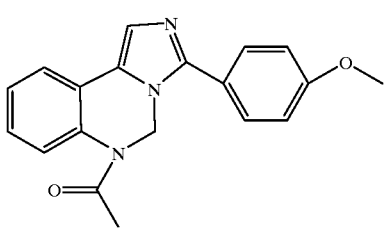
Compound 49

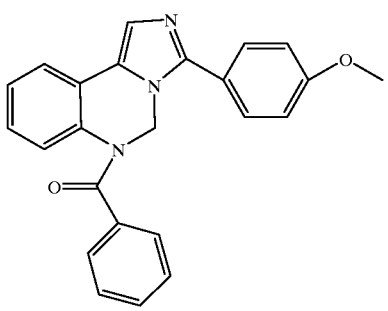
Compound 53

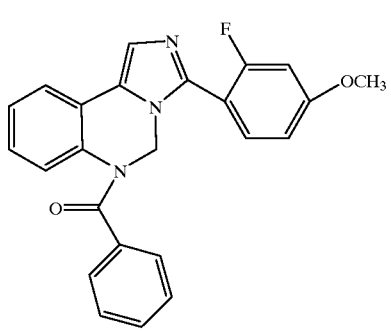
Compound 72

TABLE 1-continued

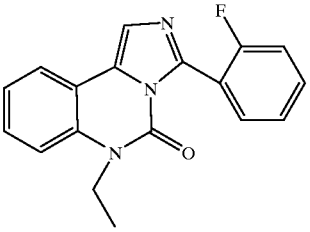
Compound 76

The pharmaceutical utility of compounds of this invention are indicated by the following assay for GABAa receptor activity.

The assay is carried out as described in Thomas and Tallman (J. Bio. Chem. 156: 9838–9842, J. Neurosci. 3:433–440, 1983). Rat cortical tissue is dissected and homogenized in 25 volumes (w/v of 0.05 M Tris HCl buffer (pH 7.4 at 4° C.). The tissue homogenate is centrifuged in the cold (4° C.) at 20,000×g for 20. minutes. The supernatant is decanted and the pellet is rehomogenized in the same volume of buffer and again centrifuged at 20,000×g. The supernatant is decanted and the pellet is frozen at −20° C. overnight. The pellet is then thawed and rehomogenized in 25 volume (original w/v) of buffer and the procedure is carried out twice. The pellet is finally resuspended in 50 volumes (w/v) of 0.05 M Tris HCl buffer (pH 7.4 at 40° C.).

Incubations contain 100 ml of tissue homogenate, 100 ml of radioligand (0.5 nM $^3$H-RO15-1788 [$^3$H-Flumazenil] specific activity 80 Ci/mmol), drug or blocker and buffer to a total volume of 500 ml. Incubations are carried for 30 min at 4° C. then are rapidly filtered through GFB filters to separate free and bound ligand. Filters are washed twice with fresh 0.05 M Tris HCl buffer (pH 7.4 at 4° C.) and counted in a liquid scintillation counter. 1.0 mM diazepam is added to some tubes to determine nonspecific binding. Data are collected in triplicate determinations, averaged and % inhibition of total specific binding is calculated. Total Specific Binding=Total−Nonspecific. In some cases, the amounts of unlabeled drugs is varied and total displacement curves of binding are carried out. Data are converted to a form for the calculation of Ki and Hill Coefficient (nH). Data for the compounds of this invention are listed in Table 2.

TABLE 2

| Compound Number[1] | Ki (nm) |
| --- | --- |
| 1 | 6 |
| 2 | 4.7 |
| 3 | 2.7 |
| 16 | 17 |
| 18 | 12 |
| 49 | 101 |
| 53 | 7.8 |
| 72 | 9.7 |
| 76 | 124 |

[1]Compound number corresponds to the compound numbers in Table 1 above as well as the compound numbers used to refer to the compounds disclosed below in the examples.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more nontoxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powers or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl momosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethyl-cellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acid, for example polyoxyethylene stearate, or condensation products of ethylene oxide with long chain aliphatic alcohols for example heptadecaethylene-oxycetanol, or condensation products of ethylene oxide with partial esters derived from fatty acids and a hexitol such as polyoxyethylene sorbitol monoleate, or condensation products of ethylene oxide with partial esters derived from fatty acids and a hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconuts oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powers and granules suitable for preparation of an aqueous suspension by the addition of water provide the active ingredient in admixture with a dispersing or wetting agent, suspending agent and one or more preservatives, Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and a hexitol, anhydrides, for example sorbitan monoleate, and condensation product of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispensing or wetting agents and suspending agents which have been mentioned above. The sterile injectable preparation may also be sterile injectable solution or suspension in a non-toxic parentally acceptable dilutent or solvent, for example a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any brand fixed oil may be employed including synthetic mono-or diglycerides. In addition fatty acid such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperature but liquid at the rectal temperature and will therefore melt in the rectum to release the drug. Such materials are cocoa butter and polyethylene glycols.

Compounds of general formula I may also be administered parentally in a sterile medium, The drug, depending on the vehicle and concentration used, can either be suspended or dissolved in the vehicle. Advantageously, adjuvants such as local anesthetics, preservatives and buffing agents can be dissolved in the vehicle.

Dosage levels of the order of from 0.1 mg to about 140 mg per kilogram of body weight per day are useful in the treatment of the above indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1mg to about 500 mg of an active ingredient.

It will be understood, however, that the specific dose level for any particular patient will depend upon a verity of factors including the activity of the specific compound employed, the age, body weight, general health, sex, diet, time of administration, route of administration, and rate of excretion, drug combination and the severity of the particular disease undergoing therapy.

An illustration of the preparation of compounds of the present invention is given in Schemes I and II. Those having skill in the art will recognize that the starting materials may be varied and additional steps employed to produce compounds encompassed by the present invention, as demonstrated by the following examples.

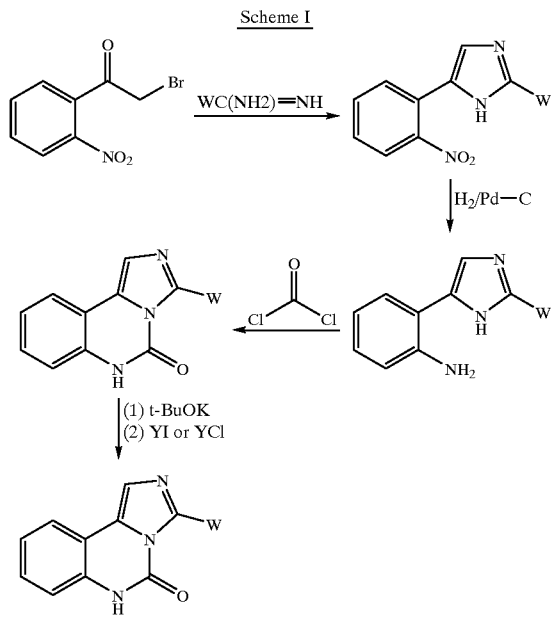

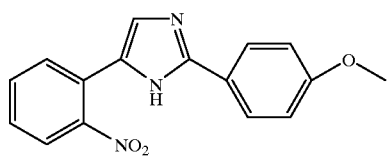

In each of Schemes I and II, the substituents Y and W are as defined above for formula I.

The disclosures in this application of all articles and references, including patents, are incorporated herein by reference.

One skilled in the art will recognize that modifications may be made in the present invention without deviating from the spirit or scope of the invention. The invention is illustrated further by the following examples which are not to be construed as limiting the invention or scope of the specific procedures or compositions described herein.

The starting materials may be obtained from commercial sources, prepared from commercially available organic compounds, or by using well known synthetic methods.

EXAMPLE I

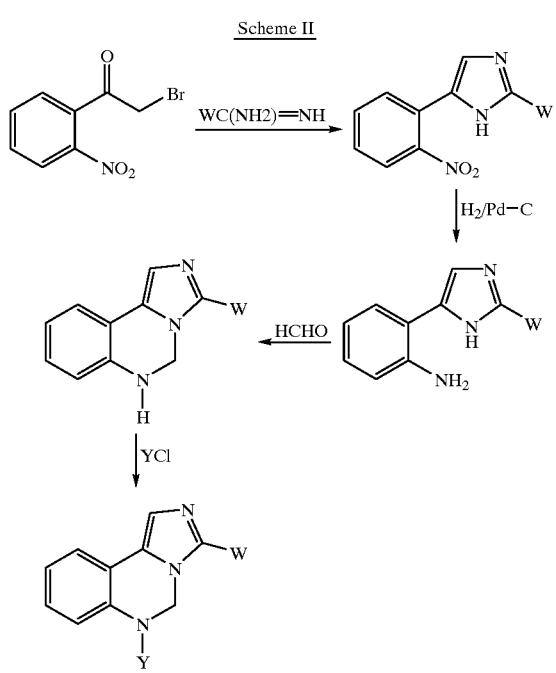

A mixture of 2-bromo-2'-nitroacetophenone (18 g), 4-methoxybenzamidine (20 g), and silica gel (20 g) in acetonitrile (500 ml) is heated at 40° C. for 24 hours. The reaction is evaporated and the residue put on a layer of silica gel and eluted with 50% ethyl acetate/hexane (1500 ml). The solution is evaporated under reduced pressure to approximately 250 ml and extracted with 5% HCl (3×250 ml). The combined aqueous solution is basified with $K_2CO_3$ and extracted with ethyl acetate (3×400 ml) to afford 2-(4-methoxyphenyl)-4-(2-nitrophenyl)-imidazole (17 g) as a dark yellow oil which is used in the next step without further purification.

EXAMPLE II

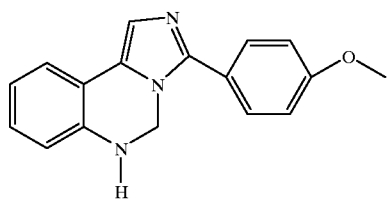

2-(4-Methoxyphenyl)-4-(2-nitrophenyl)imidazole (10 g) is mixed with EtOH (80 ml) and 5% Pd-C (wet, 2 g). The mixture is shaken under hydrogen at 50 psi for 45 min. then filtered through Celite. The filtrate is evaporated under reduced pressure to yield 2-(4-methoxyphenyl)-4-(2-aminophenyl)imidazole (9.2 g) as a brown solid which is used in the next step without further purification.

EXAMPLE III 2-(4-Methoxyphenyl)-4-(2-aminophenyl)imidazole (5 g) is dissolved in acetic acid (20 ml) and formaldehyde (37% in water, 1.53 ml) is added. The reaction is stirred for 2 min., diluted with ethyl acetate (100 ml), and extracted with 5%HCl (250 mnl). The aqueous layer is basified with K₂CO₃, then extracted with ethyl acetate. The organic layer is evaporated under reduced pressure and the residue is recrystallized from dichloromethane to afford 3-(4-methoxyphenyl)-5,6-dihydroimidazo[1,5-c]quinazoline (3 g) as a light brown solid. m.p. 190–191° C.

EXAMPLE IV

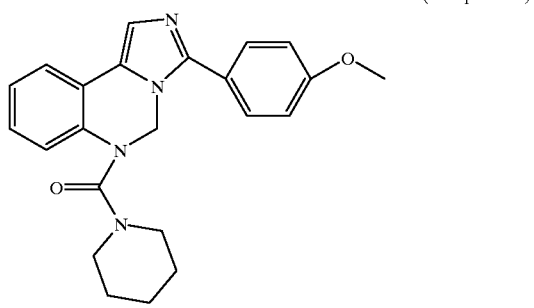

(Compound 1)

To a mixture of 3-(4-methoxyphenyl)-5,6-dihydroimnidazo[1,5-c]quinazoline (100 mg) and diisopropylethylamine (50 ml) in THF (20 ml) is added phosgene (20% in Toluene, 100 ml) and the mixture stirred at RT for 1.5 hours. The reaction is evaporated to dryness and piperidine (100 ml) in THF (20 ml) is added to the reaction vessel. The reaction is stirred for 3 min., then extracted with ethyl acetate (200 ml). The organic layer is evaporated and the residue is purified by preparative-plate chromatography (75% ethyl acetate/hexane) to afford 3-(4-methoxyphenyl)-5,6-dihydro-6-[(1-piperidino)carbonyl]imidazo[1,5-c] quinazoline (Compound 1 ) as an oil. The free base is dissolved in ether, and saturated HCl-ethyl acetate solution is added to give the hydrochloride salt. m.p. 168–170 ° C.

EXAMPLE V

The following compounds are prepared essentially according to the procedures described in Example IV:

a) 3-(4-Methoxyphenyl)-5,6-dihydro-6-[(N,N-dimethyl-arnino)carbonyl]imidazo[1,5-c]quinazoline hydrochloride (Compound 2 ).

b) 3-(4-Methoxyphenyl)-5,6-dihydro-6-[(1-morpholino)-carbonyl]imidazo[1,5-c]quinazoline hydrochloride (Compound 3). m.p. 208–211° C.

c) 3-(4 Methoxyphenyl)-5,6-dihydro-6-[(N,N-diethylamino-carbonyl]imidazo[1,5-c]quinazoline hydrochloride (Compound 4).

d) 3-(4-Methoxyphenyl)-5,6-dihydro-6-[(N,N-dipropyl-amino)carbonyl]imidazo[1,5-c]quinazoline hydrochloride (Compound 5).

e) 3-(4-Methoxyphenyl)-5,6-dihydro-6-[(N,N-dibutyl-amino)carbonyl]imidazo [1,5-c]quinazoline hydrochloride (Compound 6).

f) 3-(4-Methoxyphenyl)-5,6-dihydro-6-[(N-ethylamino)-carbonyl]imidazo[1,5-c]quinazoline hydrochloride (Compound 7).

g) 3-(4-Methoxyphenyl)-5,6-dihydro-6-[(1-pyrrolidino) carbonyl]imidazo[1,5-c]quinazoline hydrochloride (Compound 8).

h) 3-(4-Methoxyphenyl)-5,6-dihydro-6-[(1-hexamethylene-imino)carbonyl]-imidazo[1,5-c]quinazoline hydrochloride (Compound 9). m.p. 173–175° C.

i) 3-(4-Methoxyphenyl)-5,6-dihydro-6-[(1-heptamethyl-eneirnino)carbonyl]-imidazo[1,5-c]quinazoline hydrochloride (Compound 10). m.p. 197–199 ° C.

j) 3-(4-Methoxyphenyl)-5,6-dihydro-6-[(1-piperazino)-carbonyl]imidazo[1,5-c]quinazoline hydrochloride (Compound 11).

k) 3-(4-Methoxyphenyl)-5,6-dihydro-6-(1-homopiperazino-carbonyl)imidazo[1,5-c]quinazoline hydrochloride (Compound 12).

l) 3-(4-Methoxyphenyl)-5,6-dihydro-6-[1-(2,5-dimethyl-piperazino)carbonyl]imidazo[1,5-c]quinazoline hydrochloride (Compound 13).

m) 3-(4-Methoxyphenyl)-5,6-dihydro-6-[1-(3,5-dimethyl-piperazino)carbonyl]imidazo[1,5-c]quinazoline hydrochloride (Compound 14). m.p. >260° C.

n) 3-(4-Methoxyphenyl)-5,6-dihydro-6-[(4-methyl-piperazino)carbonyl]imidazo[1,5-c]quinazoline hydrochloride (Compound 15). m.p. >240° C.

o) 3-(3-Methoxyphenyl)-5,6-dihydro-6-[(1-piperidino)-carbonyl)imidazo[1,5-c]quinazoline hydrochloride (Compound 16).

p) 3-(3-Methoxyphenyl)-5,6-dihydro-6-[(1-hexamethylene-imino)carbonyl]imidazo[1,5-c]quinazoline hydrochloride (Compound 17).

q) 3-Phenyl-5,6-dihydro-6-[(1-hexamethyleneimino)-carbonyl]imidazo[1,5-c]quinazoline hydrochloride (Compound 18).

r) 3-(2-Fluorophenyl)-5,6-dihydro-6-[(N-ethylamino)-carbonyl]imidazo[1,5-c]quinazoline hydrochloride (Compound 19).

s) 3-(2-Fluorophenyl)-5,6-dihydro-6-[(N-isopropyl)-carbonyl]imidazo[1,5-c]quinazoline hydrochloride (Compound 20).

t) 3-(2-Fluoro-4-methoxyphenyl)-5,6-dihydro-6-[(1-hexa-methyleneimino)carbonyl]imidazo[1,5-c]quinazoline hydrochloride (Compound 21). m.p. 199–202° C.

u) 3-(2-Fluoro-4-methoxyphenyl)-5,6-dihydro-6-[(N-ethyl-amino)carbonyl]imidazo[1,5-c]quinazoline hydrochloride (Compound 22).

v) 3-(2-Thiophene)-5,6-dihydro-6-[(1-hexamethylene-imino)carbonyl]imidazo(1,5-c]quinazoline hydrochloride (Compound 23).

w) 3-(3-Thiophene)-5,6-dihydro-6-[(1-piperdino) carbonyl]-imidazo[1,5-c]quinazoline hydrochloride (Compound 24) m.p. 56–64° C.

x) 3-(3-Thiophene)-5,6-dihydro-6-[(1-hexamethylene-imino)carbonyl]imidazo[1,5-c]quinazoline hydrochloride (Compound 25).

y) 3-(3-Thiophene)-5,6-dihydro-6-[(1-pyrrolidino)-carbonyl]imidazo[1,5-c]quinazoline hydrochloride (Compound 26).

z) 3-(3-Thiophene)-5,6-dihydro-6-[(1-morpholino)-carbonyl]imidazo [1,5-c]quinazoline hydrochloride (Compound 27).

aa) 3-(4-Pyridyl)-5,6-dihydro-6-[(1-hexamethyleneimino)-carbonyl]imidazo[1,5-c]quinazoline hydrochloride (Compound 28).

bb) 3-(4-Pyridyl)-5,6-dihydro-6-[(1-morphofino) carbonyl]-imidazo[1,5-c]quinazoline hydrochloride (Compound 29).

cc) 3-(4-Methylphenyl)-5,6-dihydro-6-[(1-hexamethylene-imino)carbonyl]imidazo[1,5-c]quinazoline hydrochloride (Compound 30).

dd) 3-(4-Methylphenyl)-5,6-dihydro-6-[(3-pyridyl)-carbonyl]imidazo[1,5-c]quinazoline hydrochloride (Compound 31).

ee) 3-(3-Methoxyphenyl)-5,6-dihydro-6-[(1-hexamethyleneimino)carbonyl]imidazo[1,5-c]quinazoline hydrochloride (Compound 32).

ff) 3-(3-Methoxyphenyl)-5,6-dihydro-6-[(1-morpholino)-carbonyl]imidazo[1,5-c]quinazoline hydrochloride (Compound 33).

gg) 3-(3-Methoxyphenyl)-5,6-dihydro-6-[(1-pyrrolidino)-carbonyl]imidazo[1,5-c]quinazoline hydrochloride (Compound 34).

hh) 3-(3-Methoxyphenyl)-5,6-dihydro-6-[(1-piperidino)-carbonyl]imidazo[1,5-c]quinazoline hydrochloride (Compound 35).

ii) 3-(3-Methoxyphenyl)-5,6-dihydro-6-[(3-pyridyl)-carbonyl]imidazo[1,5-c]quinazoline hydrochloride (Compound 36).

jj) 3-(3-Methoxyphenyl)-5,6-dihydro-6-[phenylcarbonyl]-imidazo[1,5-c]quinazoline hydrochloride (Compound 37).

kk) 3-(3-Methoxyphenyl)-5,6-dihydro-6-[(3-fluorophenyl)-carbonyl]imidazo[1,5-c]quinazoline hydrochloride (Compound 38).

ll) 3-(3-Methoxyphenyl)-5,6-dihydro-6-[(N,N-dimethylamino)carbonyl]imidazo[1,5-c]quinazoline hydrochloride (Compound 39).

mm) 3-(3-Methoxyphenyl)-5,6-dihydro-6-[(N,N-diethylarnino)carbonyl]imidazo[1,5-c]quinazoline hydrochloride (Compound 40).

nn) 3-Phenyl-5,6-dihydro-6-[(N,N-diethylamino)carbonyl]-imidazo[1,5-c]quinazoline hydrochloride (Compound 41).

oo) 3-Phenyl-5,6-dihydro-6-[(1-pyrrolidino)carbonyl]-imidazo[1,5-c]quinazoline hydrochloride (Compound 42).

pp) 3-Phenyl-5,6-dihydro-6-[(1-piperidino)carbonyl]-imidazo[1,5-c]quinazoline hydrochloride (Compound 43).

qq) 3-Phenyl-5,6-dihydro-6-[(1-morpholino)carbonyl]-imidazo[1,5-c]quinazoline hydrochloride (Compound 44).

rr) 3-Phenyl-5,6-dihydro-6-[(1-heptamethyleneimnino)-carbonyl]imidazo[1,5-c]quinazoline hydrochloride (Compound 45). m.p. 230–233° C.

ss) 3-Phenyl-5,6-dihydro-6-[cyclopropylcarbonyl]-imidazo[1,5-c]quinazoline hydrochloride (Compound 46).

tt) 3-Phenyl-5,6-dihydro-6-[cyclohexylcarbonyl]-imidazo[1,5-c]quinazoline hydrochloride (Compound 47).

uu) 3-Phenyl-5,6-dihydro-6-[(2-thiophene)carbonyl]-imidazo[1,5-c]quinazoline hydrochloride (Compound 48).

EXAMPLE VI (Compound 49)

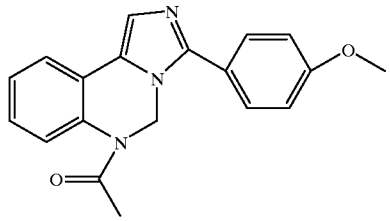

To a mixture of 3-(4-methoxyphenyl)-5,6-dihydroimidazo[1,5-c]quinazoline (100 mg) and diisopropylethylamine (50 ml) in THF (20 ml) is added acetyl chloride (50 ml) and the mixture stirred at RT for 5 hours. The reaction is extracted with ethyl acetate (200 ml), the solvent evaporated, and the residue is purified by preparative-plate chromatography (75% ethyl acetate/hexane) to afford 3-(4-methoxyphenyl)-5,6-dihydro-6-acetylimidazo[1,5-c]-quinazoline (Compound 49) as a light yellow solid . m.p. 80–82° C.

EXAMPLE VII (Compound 50)

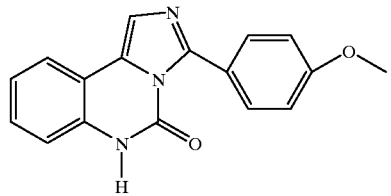

Phosgene (20% in Toluene, 150 ml) is added slowly to a mixture of 2-(4-methoxyphenyl)-4-(2-aminophenyl) imidazole (250 mg) and diisopropylethylamine (100 ml) in THF (25 ml). The reaction is allowed to stir at RT for 5 min., then extracted with ethyl acetate (300 ml). The organic layer is evaporated and the residue is recrystallized from ethanol to afford 3-(4-methoxyphenyl)-5,6-dihydro-5-oxo-[6H]imidazo[1,5-c]-quinazoline (Compound 50) as a white solid, m.p. 267–268° C.

EXAMPLE VIII (Compound 51)

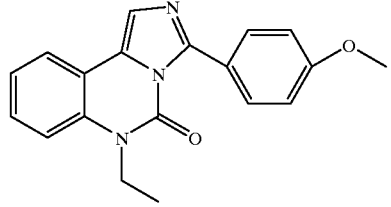

To 3-(4-methoxyphenyl)-5,6-dihydro-5-oxo-[6H]-imidazo [1,5-c]quinazoline(100 mg) dissolved in DMF (5 ml) is added potassium t-butoxide (1 M in THF, 250 ml). After stirring for 30 min, iodoethane (100 ml) is added, and the mixture is allowed to stand at room temperature for 24 hours. The reaction is extracted with ethyl acetate and the organic layer evaporated under reduced pressure to appoximately 3 ml. Saturated HCl-ethyl acetate solution is added, and the precipitate filtered to afford 3-(4-methoxy-phenyl)-5,6-dihydro-5-oxo-6-ethylimidazo[1,5-c]quinazoline hydrochloride as a yellow solid (Compound 51). m.p.>170° C.

EXAMPLE IX

The following compounds are prepared essentially according to the procedures described in Examples VI–VIII:

a) 3-(4-Methoxyphenyl)-5,6-dihydro-6-(1-propionyl)-imidazo[1,5-c]quinazoline (Compound 52). m.p. 165–167° C.

b) 3-(4-Methoxyphenyl)-5,6-dihydro-6-benzoylimidazo-[1,5-c]quinazoline (Compound 53).

c) 3-(4-Methoxyphenyl)-5,6-dihydro-6-(4-chlorobenzoyl)-imidazo[1,5-c]quinazoline hydrochloride (Compound 54).

d) 3-(4-Methoxyphenyl)-5,6-dihydro-6-(4-methoxybenzoyl)imidazo[1,5-c]quinazoline hydrochloride (Compound 55).

e) 3-(4-Methoxyphenyl)-5,6-dihydro-6-(4-fluorobenzoyl)-imidazo[1,5-c]quinazoline hydrochloride (Compound 56). m.p. 251–254° C.

f) 3-(4-Methoxyphenyl)-5,6-dihydro-6-(3-fluorobenzoyl)-imidazo[1,5-c]quinazoline (Compound 57).

g) 3-(4-Methoxyphenyl)-5,6-dihydro-6-(2-fluorobenzoyl)-imidazo[1,5-c]quinazoline (Compound 58).

h) 3-(4-Methoxyphenyl)-5,6-dihydro-6-(4-methylbenzoyl)-imidazo[1,5-c]quinazoline (Compound 59).

i) 3-(4-Methoxyphenyl)-5,6-dihydro-6-(3-methylbenzoyl)-imidazo[1,5-c]quinazoline (Compound 60).

j) 3-(4-Methoxyphenyl)-5,6-dihydro-6-(2-methylbenzoyl)-imidazo[1,5-c]quinazoline (Compound 61).

k) 3-(4-Methoxyphenyl)-5,6-dihydro-6-(4-ethylbenzoyl)-imidazo[1,5-c]quinazoline (Compound 62).

l) 3-(4-Methoxyphenyl)-5,6-dihydro-6-(3-fluoro-2-methylbenzoyl)imidazo[1,5-c]quinazoline (Compound 63).

m) 3-(4-Methoxyphenyl)-5,6-dihydro-6-(3-fluoro-4-methylbenzoyl)imidazo[1,5-c]quinazoline (Compound 64).

n) 3-(4-Methoxyphenyl)-5,6-dihydro-6-(2,3-dimethylbenzoyl)imidazo[1,5-c]quinazoline (Compound 65).

o) 3-(4-Methoxyphenyl)-5,6-dihydro-6-(2,4-dimethylbenzoyl)imidazo[1,5-c]quinazoline (Compound 66).

p) 3-(4-Methoxyphenyl)-5,6-dihydro-6-(2,5-dimethylbenzoyl)imidazo[1,5-c]quinazoline (Compound 67).

q) 3-(4-Methoxyphenyl)-5,6-dihydro-6-(3,4-dimethylbenzoyl)imidazo[1,5-c]quinazoline (Compound 68).

r) 3-(4-Methoxyphenyl)-5,6-dihydro-6-(3,5-dimethylbenzoyl)imidazo[1,5-c]quinazoline (Compound 69).

s) 3-(4-Methoxyphenyl)-5,6-dihydro-6-(2-methoxybenzoyl)imidazo[1,5-c]quinazoline (Compound 70).

t) 3-(4-Methoxyphenyl)-5,6-dihydro-6-(3-methoxybenzoyl)imidazo[1,5-c]quinazoline (Compound 71).

u) 3-(2-Fluoro-4-methoxyphenyl)-5,6-dihydro-6-benzoyl-imidazo[1,5-c]quinazoline (Compound 72). m.p. 196–197° C.

v) 3-(2-Fluoro-4-methoxyphenyl)-5,6-dihydro-6-acetyl-imidazo[1,5-c]quinazoline hydrochloride (Compound 73). m.p. 113–116° C.

w) 3-(2-Fluorophenyl)-5,6-dihydro-5-oxo-[6H]imidazo[1,5-c]quinazoline. (Compound 74).

x) 3-Phenyl-5,6-dihydro-5-oxo-[6H]imidazo[1,5-c]-quinazoline (Compound 75). m.p. 280–283° C.

y) 3-(2-Fluorophenyl)-5,6-dihydro-5-oxo-6-ethyl-imidazo[1,5-c]quinazoline (Compound 76).

z) 3-(2-Fluorophenyl)-5,6-dihydro-5-oxo-6-isopropyl-imidazo[1,5-c]quinazoline (Compound 77).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of the formula:

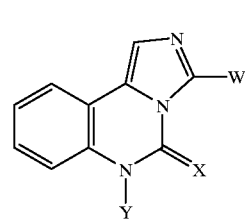

or the pharmaceutically acceptable nontoxic salts thereof wherein:

X is oxygen or $H_2$;

Y is hydrogen, alkyl, alkenyl, (substituted)arylalkyl, alkoxycarbonyl, acyl, aroyl, alkoxyalkyl, alkoxy, alkylamino-carbonyl, cycloalkylaminocarbonyl, aryl or heteroaryl each of which is optionally substituted with halogen, lower alkyl, amino lower alkyl, or lower alkoxy; and W is phenyl, thienyl, or pyridyl, each of which is optionally substituted with up to two groups independently selected from halogen, hydroxy, lower alkyl, or lower alkoxy having 1–6 carbon atoms, amino, or mono- or dialkylamino where each alkyl is independently lower alkyl.

2. A compound according to claim 1, which is 3-(4-methoxyphenyl)-5,6-dihydro-6-[(1-piperidino) carbonyl]imidazo[1,5-c]-quinazoline;

3-(4-methoxy-phenyl)-5,6-dihydro-6-[(N,N-dimethylamino) carbonyl]-imidazo[1,5-c]quinazoline, 3-(4-methoxy-phenyl)-5,6-dihydro-6-[(1-morpholino)-carbonyl]imidazo[1,5-c]quinazoline;

3-(4-methoxyphenyl)-5,6-dihydro-6-[(N,N-diethylamino-carbonyl]-imidazo[1,5-c]quinazoline;

3-(4-methoxyphenyl)-5,6-dihydro-6-[(N,N-dipropylamino)carbonyl]-imidazo[1,5-c]quinazoline;

3-(4-methoxyphenyl)-5,6-dihydro-6-[(N,N-dibutylamino)carbonyl]-imidazo[1,5-c]quinazoline;

3-(4-methoxyphenyl)-5,6-dihydro-6-[(N-ethylamino) carbonyl]imidazo[1,5-c]quinazoline;

3-(4-methoxyphenyl)-5,6-dihydro-6-[(1-pyrrolidino) carbonyl]imidazo[1,5-c]quinazoline;

3-(4-methoxyphenyl)-5,6-dihydro-6-[(1-hexamethyleneimino)carbonyl]-imidazo[1,5-c] quinazoline; or 3-(4-methoxyphenyl)-5,6-dihydro-6-[(1-heptamethyleneimino)carbonyl]-imidazo[1,5-c] quinazoline.

3. A compound according to claim 1, which is 3-(4-methoxyphenyl)-5,6-dihydro-6-[(1-piperazino) carbonyl]imidazo[1,5-c]quinazoline;

3-(4-methoxyphenyl)-5,6-dihydro-6-(1-homopiperazinocarbonyl)-imidazo[1,5-c]quinazoline;

3-(4-methoxyphenyl)-5,6-dihydro-6-[1-(2,5-dimethylpiperazino)carbonyl]-imidazo[1,5-c] quinazoline;

3-(4-methoxyphenyl)-5,6-dihydro-6-[1-(3,5-dimethylpiperazino)carbonyl]-imidazo[1,5-c] quinazoline;

3-(4-methoxyphenyl)-5,6-dihydro-6-[(4-methylpiperazino)carbonyl]-imidazo[1,5-c] quinazoline;

3-(3-methoxyphenyl)-5,6-dihydro-6-[(1-piperidino)carbonyl]imidazo[1,5-c]quinazoline;

3-(3-methoxyphenyl)-5,6-dihydro-6-[(1-hexamethyleneimino)carbonyl]-imidazo[1,5-c]quinazoline;

3-phenyl-5,6-dihydro-6-[(1-hexamethyleneimino)carbonyl]imidazo[1,5-c]-quinazoline;

3-(2-fluorophenyl)-5,6-dihydro-6-[(N-ethylamino)carbonyl]imidazo[1,5-c]-quinazoline; or 3-(2-fluorophenyl)-5,6-dihydro-6-[(N-isopropyl)carbonyl]imidazo[1,5-c]-quinazoline.

4. A compound according to claim 1 which is 3-(2-fluoro-4-methoxyphenyl)-5,6-dihydro-6-[(1-hexamethyleneimino)-carbonyl]imidazo[1,5-c]quinazoline;

3-(2-fluoro-4-methoxyphenyl)-5,6-dihydro-6-[(N-ethylamino)carbonyl]-imidazo[1,5-c]quinazoline;

3-(2-thiophene)-5,6-dihydro-6-[(1-hexamethyleneimino)carbonyl]imidazo[1,5-c]quinazoline;

3-(3-thiophene)-5,6-dihydro-6-[(1-piperdino)carbonyl]imidazo[1,5-c]quinazoline;

3-(3-thiophene)-5,6-dihydro-6-[(1-hexamethyleneimino)carbonyl]imidazo[1,5-c]quinazoline;

3-(3-thiophene)-5,6-dihydro-6-[(1-pyrrolidino)carbonyl]imidazo[1,5-c]-quinazoline;

3-(3-thiophene)-5,6-dihydro-6-[(1-morpholinocarbonyl]imidazo[1,5-c]-quinazoline;

3-(4-pyridyl)-5,6-dihydro-6-[(1-hexamethyleneimino)carbonyl]imidazo[1,5-c]-quinazoline;

3-(4-pyridyl)-5,6-dihydro-6-[(1-morpholino)carbonyl]imidazo[1,5-c]quinazoline; or 3-(4-methylphenyl)-5,6-dihydro-6-[(1-hexamethyleneimino)carbonyl]-imidazo[1,5-c]quinazoline.

5. A compound according to claim 1 which is 3-(4-methylphenyl)-5,6-dihydro-6-[(3-pyridyl)carbonyl]imidazo[1,5-c]-quinazoline;

3-(3-methoxyphenyl)-5,6-dihydro-6-[(1-hexamethyleneimino)carbonyl]-imidazo[1,5-c]quinazoline;

3-(3-methoxy-phenyl)-5,6-dihydro-6-[(1-morpholino)carbonyl]imidazo[1,5-c]quinazoline;

3-(3-methoxyphenyl)-5,6-dihydro-6-[(1-pyrrolidino)carbonyl]imidazo[1,5-c]quinazoline;

3-(3-methoxyphenyl)-5,6-dihydro-6-[(1-piperidino)carbonyl]imidazo[1,5-c]-quinazoline;

3-(3-methoxyphenyl)-5,6-dihydro-6-[(3-pyridyl)carbonyl]imidazo[1,5-c]-quinazoline;

3-(3-methoxyphenyl)-5,6-dihydro-6-benzoyl-imidazo[1,5-c]-quinazoline;

3-(3-methoxyphenyl)-5,6-dihydro-6-[(3-fluorophenyl)carbonyl]imidazo-[1,5-c]quinazoline;

3-(3-methoxyphenyl)-5,6-dihydro-6-[(N,N-dimethylamino)carbonyl]-imidazo[1,5-c]quinazoline; or 3-(3-methoxyphenyl)-5,6-dihydro-6-[(N,N-diethylamino)carbonyl]imidazo-[1,5-c]quinazoline.

6. A compound according to claim 1 which is 3-phenyl-5,6-dihydro-6-[(N,N-diethylamino)carbonyl]imidazo[1,5-c]-quinazoline;

3-phenyl-5,6-dihydro-6-[(1-pyrrolidino)carbonyl]imidazo[1,5-c]quinazoline;

3-phenyl-5,6-dihydro-6-[(1-piperidino)carbonyl]imidazo[1,5-c]quinazoline;

3-phenyl-5,6-dihydro-6-[(1-morpholino)carbonyl]imidazo[1,5-c]quinazoline;

3-phenyl-5,6-dihydro-6-[(1-heptamethyleneimino)carbonyl]imidazo[1,5-c]-quinazoline;

3-phenyl-5,6-dihydro-6-[cyclopropylcarbonyl]imidazo[1,5-c]quinazoline;

3-phenyl-5,6-dihydro-6-[cyclohexylcarbonyl]imidazo[1,5-c]quinazoline;

3-phenyl-5,6-dihydro-6-[(2-thiophene)carbonyl]imidazo[1,5-c]quinazoline, 3-(4-phenyl)-5,6-dihydro-5-oxo-6-ethylimidazo[1,5-c]quinazoline; or 3-(4-methoxyphenyl)-5,6-dihydro-6-(4-chlorobenzoyl)imidazo[1,5-c]-quinazoline.

7. A compound according to claim 1 which is 3-(4-methoxyphenyl)-5,6-dihydro-6-(4-methoxybenzoyl)imidazo[1,5-c]-quinazoline;

3-(4-methoxyphenyl)-5,6-dihydro-6-(4-fluorobenzoyl)imidazo[1,5-c]-quinazoline; or 3-(2-fluoro-4-methoxyphenyl)-5,6-dihydro-6-acetylimidazo[1,5-c]-quinazoline.

8. A method for treatment of anxiety which comprises administering to a patient in need of such treatment an effective amount of a compound according to claim 1.

9. A method for treatment of sleep disorders, which comprises administering to a patient in need of such treatment an effective amount of a compound according to claim 1.

10. A method for treatment of seizure disorders, which comprises administering to a patient in need of such treatment an effective amount of a compound according to claim 1.

11. A method for treatment of overdose with benzodiazepine drugs, which comprises administering to a patient in need of such treatment an effective amount of a compound according to claim 1.

12. A method for enhancement of memory which comprises administering to a patient in need of such treatment an effective amount of a compound according to claim 1.

* * * * *